(12) United States Patent
Wisniewski

(10) Patent No.: US 8,281,785 B2
(45) Date of Patent: Oct. 9, 2012

(54) BREATHING SYSTEM

(76) Inventor: Pawel Wisniewski, Glenwood (ZA)

( * ) Notice: Subject to any disclaimer, the term of this patent is extended or adjusted under 35 U.S.C. 154(b) by 1079 days.

(21) Appl. No.: 11/913,027

(22) PCT Filed: Apr. 28, 2006

(86) PCT No.: PCT/ZA2006/000061
§ 371 (c)(1),
(2), (4) Date: Jun. 25, 2008

(87) PCT Pub. No.: WO2006/119515
PCT Pub. Date: Nov. 9, 2006

(65) Prior Publication Data
US 2009/0205653 A1 Aug. 20, 2009

(30) Foreign Application Priority Data

Apr. 29, 2005 (ZA) .................................. 2005/03437

(51) Int. Cl.
*A61M 16/00* (2006.01)
(52) U.S. Cl. .......... 128/203.28; 128/202.27; 128/205.14
(58) Field of Classification Search ............ 128/202.27, 128/202.28, 202.29, 203.11, 203.12, 203.13, 128/203.28, 205.13, 205.14, 205.15, 205.16, 128/205.17, 910, 911, 912
See application file for complete search history.

(56) References Cited

U.S. PATENT DOCUMENTS

| | | | | |
|---|---|---|---|---|
| 5,507,280 A * | 4/1996 | Henkin et al. | ........... | 128/203.12 |
| 5,598,840 A * | 2/1997 | Iund et al. | ................ | 128/207.14 |
| 6,206,002 B1 * | 3/2001 | Lambert | .................. | 128/205.12 |
| 6,648,832 B2 * | 11/2003 | Orr et al. | ........................ | 600/532 |
| 2004/0094156 A1 * | 5/2004 | Meakin | .................... | 128/205.13 |
| 2005/0188990 A1 * | 9/2005 | Fukunaga et al. | ........ | 128/204.18 |
| 2009/0301484 A1 * | 12/2009 | Dunlop | .................... | 128/203.12 |
| 2011/0030688 A1 * | 2/2011 | Meakin | .................... | 128/205.13 |

* cited by examiner

*Primary Examiner* — Glenn Richman
(74) *Attorney, Agent, or Firm* — Wyatt, Tarrant & Combs, LLP; H. Roy Berkenstock

(57) ABSTRACT

Breathing equipment (10) for use in conventional operating room procedures comprises a flexible breathing bag (12) connected at one end (12.1) via a gas redirecting connector (14) to a gas guiding tube (16) and at the opposite end to a flexible exhaust gas bridging tube (18) forming part of a gas removal conduit (20) used for the remote venting of exhaled gas via a remote discharge tube (22) also forming part of the conduit (20). A breathing piece (28) is situated at the free end of the tube (16). An inhalation gas supply tube (24) passes within the tube (22) and via the connector (14) into the gas guiding tube (16) up to a position of discharge in close proximity of a user. The connector (14) is formed to cause exhaled gases from the piece (28) to pass along the tube (16) and through the bag (12) prior to remote venting to enable use of the 'feel' of the bag (12) during breathing assistance.

6 Claims, 2 Drawing Sheets

BREATHING SYSTEM

CROSS-REFERENCE TO RELATED APPLICATIONS

This application relates to and claims priority of ZA 2005/03437 filed Apr. 29, 2005 and PCT-ZA 2006/000061 filed Apr. 28, 2006

STATEMENT REGARDING FEDERALLY SPONSORED RESEARCH OR DEVELOPMENT

Not applicable

REFERENCE TO A MICROFICHE APPENDIX

Not applicable.

BACKGROUND TO THE INVENTION

Breathing equipment for use in anaesthesiology procedures is common in the art. The conventional breathing bag consists of a breathing bag to which a tube at the remote end carrying a breathing piece is fitted, is connected. Inhalation gas is introduced remote from the breathing piece (sometimes breathing gas can be introduced directly to the breathing piece) into the tube while the discharge from the bag is directly to its environment of use thus contaminating it during use of the equipment. As a development to remote discharge from the bag for remote venting the discharge has been fitted with a tube to which a suction is applied while the tube is formed with apertures to lessen the vacuuming effect to have the bag retaining its 'feel'. This variation to the basic equipment has the drawback that it is clumsy to use while the effect of the suction pump impedes the 'feel' of the bag. A further development as amongst others described in NZ patent number 525090 uses two bags the one fitted within the other with the discharge from the inner bag communicating with the outer bag while exhaust gas is discharged along a annular zone formed between a sleeve forming part of the outer bag fitting onto the breathing piece to breathing bag flow tube. While this development effectively enables the remote discharge of exhaled gas the double bag configuration results in a loss of bag 'feel'. Another solution is to fit the bag with a valve attachable to a tubing remotely discharging gases. Although this is popular solution it makes equipment balky and presence of a valve is not always desirable.

FIELD OF THE INVENTION

This invention relates to breathing equipment at least employable for use in anaesthesiology procedure and to a breathing equipment set. Although not so limited the invention finds particular application during the performance of conventional anaesthesiology procedure in an operating theatre or the like.

PRIOR ART DESCRIPTION

Breathing equipment for use in anaesthesiology procedures is common in the art. The conventional breathing bag consists of a breathing bag to which a tube at the remote end carrying a breathing piece is fitted, is connected. Inhalation gas is introduced remote from the breathing piece into the tube while the discharge from the bag is directly to its environment of use thus contaminating it during use of the equipment. As a development to remote discharge from the bag for remote venting the discharge has been fitted with a tube to which a suction is applied while the tube is formed with apertures to lessen the vacuuming effect to have the bag retaining its 'feel'. This variation to the basic equipment has the drawback that it is clumsy to use while the effect of the suction pump impedes the 'feel' of the bag. A further development as amongst others described in NZ patent number 525090 uses two bags the one fitted within the other with the discharge from the inner bag communicating with the outer bag while exhaust gas is discharged along a annular zone formed between a sleeve forming part of the outer bag fitting onto the breathing piece to breathing bag flow tube. While this development effectively enables the remote discharge of exhaled gas the double bag configuration results in a loss of bag 'feel'.

BRIEF DESCRIPTION OF THE DRAWINGS

The invention is now described, by way of example, with reference to the accompanying drawings. In the drawings.

DETAILED DESCRIPTION OF THE DRAWINGS

Figure 1:
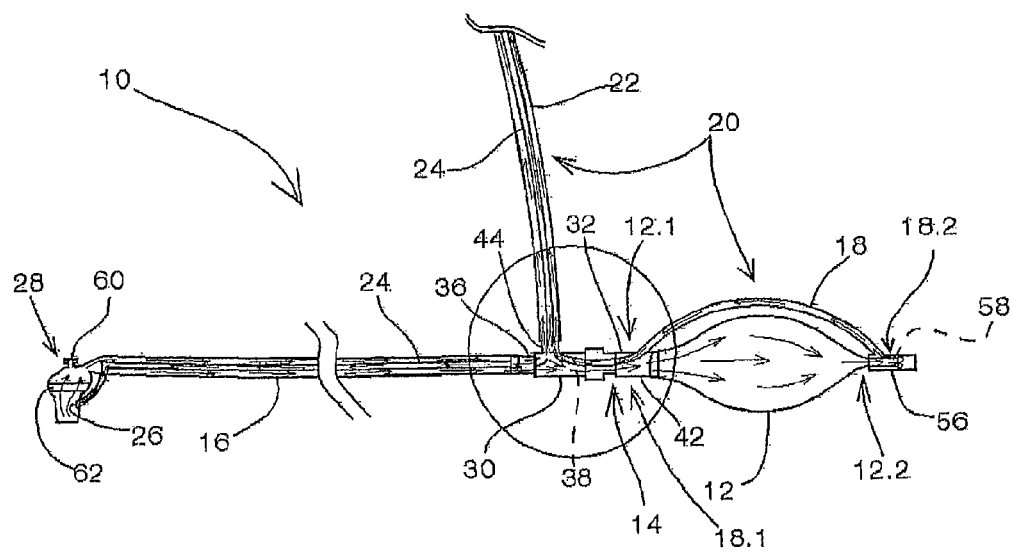
FIG. 1 shows a diagrammatical cross-sectional view of one potential embodiment of the inventive breathing equipment.
Figure 2:
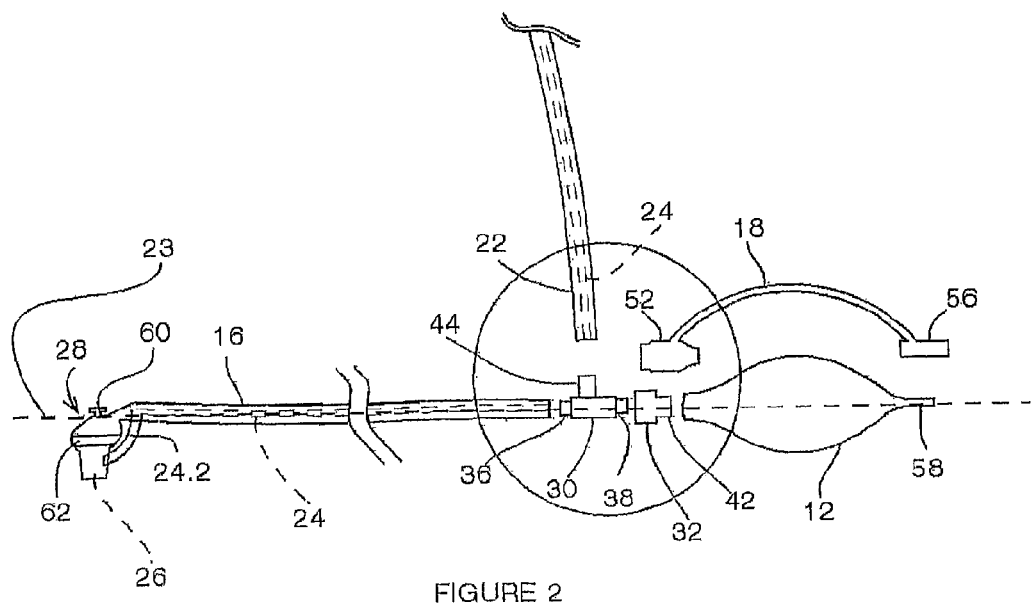
FIG. 2 shows the re-breathing equipment of FIG. 1 in exploded view.

Referring to FIGS. 1 to 4 of the drawings breathing equipment, according to the invention, composed from a set, also according to the invention, in the form of a conventional operating room employable breathing equipment, is generally indicated by reference numeral 10.

Figure 5:
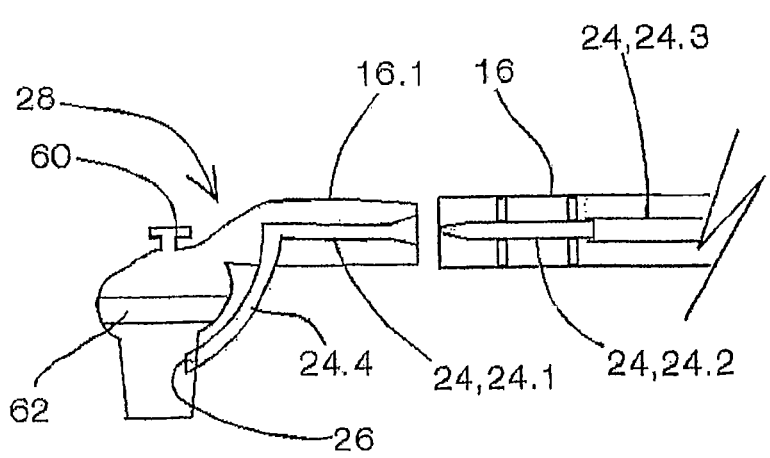
FIG. 5 shows a diagrammatic side elevational view of the breathing piece of the equipment of FIG. 1.

The equipment 10 comprises an ovally shaped latex type flexible breathing bag 12 connected at one end 12.1 via a gas redirecting connector 14 to a gas guiding conduit in the form of a flexible concertina type gas guiding tube 16 and at the opposite or distal end 12.2 to an exhaust air discharge bridging conduit in the form of a flexible bridging tube 18 forming part of a gas removal conduit 20 constituted from the tube 18 and an exhaust conduit in the form of an exhaled gas remote discharge tube 22 joining and extending laterally from the connector 14 thus remote from the patient connecting end of the tube 16. The equipment 10 also includes an inhalation oxygen and anaesthetic agent supply conduit in the form of a supply tube 24 passing within the remote discharge tube 22 and along the gas guiding tube 16 up to a position of discharge 26 situated within a breathing piece 28, also as shown in FIG. 5, carried on the outer end of the tube 16. The various tubes 18, 20, 22, 24 are geometrically inter-arranged to facilitate the ease of use of the equipment 10 under conventional conditions of breathing assistance while promoting the conventional way of use of the breathing bag 12. To this effect the gas guiding tube 16 and the breathing bag 12 are spaced along a common central line 23 while the exhaled gas remote discharge tube 22 extends laterally from the connector 14.

Figure 3:
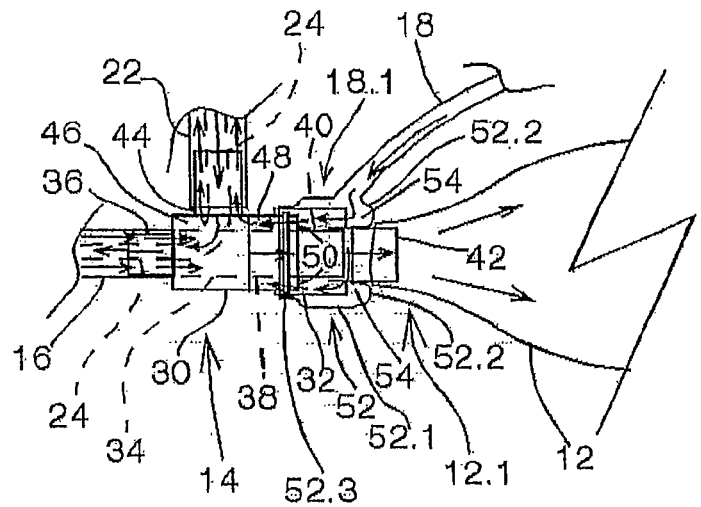
FIG. 3 shows in detail the circled central part of FIG. 1.
Figure 4:
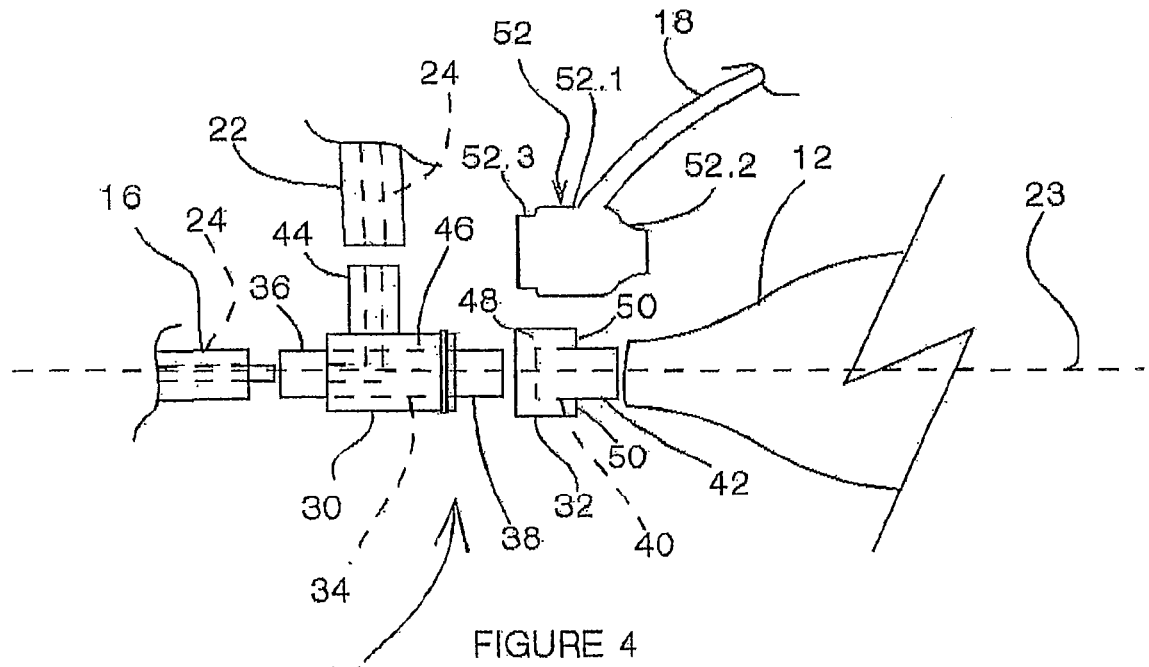
FIG. 4 shows in detail the circled central part of FIG. 2.

Referring more particularly to FIGS. 3 and 4 the connector 14 is constituted from a gas guiding and exhaust conduit connecting piece 30 removably socketing to a bridging conduit return end and breathing bag inlet aperture connecting piece 32. The piece 30 is formed with a central gas transferring passage 34 extending between a guiding tube connecting spigot 36 and an intermediate spigot 38 socketing into a breathing bag discharging passage 40 formed along the connecting piece 32 of which the end spigot 42 engages with the breathing bag 12 by the inlet aperture thereto tightly elastically fitting onto the end spigot 42. The piece 30 is also formed with an exhaust conduit connecting spigot 44 via which the tube 22 is connected thereto. The supply tube 24, as running along the remote discharge tube 22, passes along the spigots 44 and 36 from there extending along within the gas guiding tube 16 up to its position of discharge 26.

The spigot 44 opens up into an outer zone 46 extending co-axially with the passage 34 along the piece 30 while passing into a matching zone 48 along the piece 32 extending part of the length of the passage 40 co-axially along its outside. The zone 48 opens up to the environment via a set of circumferentially arranged apertures 50 (not shown in detail) by means of which the return end 18.1 of the bridging tube 18 communicates with the remote discharge tube 22.

The end 18.1 of the bridging tube 18 is in the form of a flexible stepped sleeve 52 with an inner end sleeve portion that is integrally formed with the remainder of the tube 18. The sleeve 52 is formed by a central section 52.1 ending in a sleeve 52.2 at the one side and a stepped down end section 52.3 at the opposite side. The central section 52.1 fits the piece 32 in an exhaust gas transfer chamber 54 defining fashion defined between the sleeve 52.2, as being sealably inwardly backward folded over fitted onto the piece 32 on operative fitting of the sleeve 52, thus circumferentially pinching onto the end spigot 42, and the apertures 50. The stepped down section 52.3 tightly fits the trailing end of the piece 32 thus limiting the possibility of exhaust gas escaping directly to the environment from the connector 14.

The end 18.2 of the bridging tube 18 remote from its end 18.1 is in the form of a pouch 56 that removably through against the environmental loss of exhaust gas from the re-breathing bag 12 fits a breathing bag discharge tube 58. This enables the rapid conversion of the equipment 10 to conventional re-breathing equipment in which exhaled air is discharged to the immediate environment if so desired. The advantage of disconnection of the pouch 56 lies in the ability of converting the equipment 10 to equipment that does not incorporate a gas scavenger where, for example, occlusion to the tube 58 is found.

The equipment 10 can also easily be adapted by its connection to other respiratory equipment via the spigot 38 once the piece 32 has been disconnected.

While the breathing piece 28 can be in the form of a conventional breathing mask (not shown) it can also be in the form of a unit incorporating the end sections 16.1 and 24.1 of the gas guiding tube 16 and the supply tube 24 respectively that socket into the remainders thereof on assembly of the equipment 10, as shown in FIG. 5. The end part 24.2 of the upstream extending section 24.3 of the supply tube 24 sprung fashion fits the section 24.3 to promote a sealing fit of the various sections of the tube 24 on fitment of the breathing piece 28. The breathing piece is conveniently also fitted with a carbon dioxide sampling point 60.

Even though not necessarily essential for the proper operation of the equipment 10 though in a useful additional embodiment the breathing piece 28 can incorporate a filter 62 that is situated upstream of the position of release 26 of the supply tube 24. One way of achieving such layout is to arrange the very leading end section 24.4 of the tube 24 to bypass the filter 60, as shown in FIG. 5. This layout ensures the unobstructed supply of oxygen and agent to a patient while filtering exhaled air. Part of the reason for so filtering exhaled air is because part of such air is again inhaled during subsequent inhalation by a patient in conjunction with the supply of oxygen and agent from the supply tube 24. The filter also promotes the retention of moisture in the air that is inhaled by a patient. In the case of including the filter 62 the sampling point 60 will naturally be connected to sample air prior to filtering and thus between the mouth of a user and the filter by way of a sampling tube bypass (not shown).

While the equipment 10 is composed from a variety of set pieces the invention also extends to a set consisting of the re-breathing bag 12 the bridging tube 18, the connector 14 in the form of its pieces 30 and 32, the gas guiding tube 16 and the breathing piece 28. As the supply tube 24 is in the form of conventional flexible plastic tubing it need not form part of the set though can be incorporated. The same applies to the remote discharge tube 22.

In use the equipment 10 is thus conventionally used as breathing aid in closely monitoring the breathing action of an anaesthestisized patient while also assisting with the breathing process when required. For preparation the various set pieces are thus interconnected while the supply tube 24 is inserted along the remote discharge tube 22, though the interconnected pieces 30 and 32 and down the gas guiding tube 16 up to its position of discharge within the breathing piece 28. The supply tube is naturally also connected to the conventional oxygen supply of the environment where the equipment is in use while the remote discharge tube 22 is connected for remote discharging of the exhaled gas.

The equipment 10 is conventionally used on a patient during anaesthesia with the advantage that exhaled gas is removed from the environment of use of the equipment thus preventing contamination of the air in that environment. This is achieved while retaining the manual sensitive feel of the re-breathing bag that serves as indication of the breathing effort of the patient in deciding to assist in such effort by gently compressing and releasing the bag 12 by way of a pump action. During the use of the equipment 10 when fitted with a filter, exhaled gas is filtered thus limiting breathing equipment contamination by exhaled gases and consequently the intake of pure exhaled air in conjunction with oxygen and agent during inhalation.

The invention claimed is:

1. Breathing equipment (10) at least employable for use in anesthesiology procedure comprising:
 a regularly shaped breathing bag (12) of which its location of discharging of exhaled gas (12.2) is situated remote from its location (12.1) via which it is indirectly connectable to a patient and which is accordingly of a suitably flexible material to at least enable manually assisting in the breathing process of such patient during use of the equipment (10) in response to its manual compression and relaxation;
 a gas-guiding conduit (16, 34, 40) extending between a breathing piece (28) via which gas is inhaled and exhaled by a patient during use of the equipment and the location (12.1) of the breathing bag (12);
 a supply conduit (24) via which inhalation gas in the form of air or oxygen and, where applicable, agent is introduced for inhalation by such patient via the breathing piece (28) and of which supply conduit (24) part extends within at least part of gas guiding conduit (16, 34, 40) towards said breathing piece (28) while its discharge end (26) is located in substantial proximity of the breathing location of a person on whom said equipment is used, thereby making inhalation gas directly available once the equipment is so in use;
 a gas removal conduit (20) via which exhaled gas is discharged and said supply conduit (24) and part of the gas removal conduit (20) run along a common central line (23) and, within the gas guiding conduit (16, 34, 40) at least in part;

characterized in that the gas removal conduit (20) returning in snug adjacent relationship with the breathing bag (12) from its location of discharging of exhaled gas (12.2) to the vicinity of the location (12.1) via which it is indirectly connectable to a patient in a way that maintains proper access to the manual manipulation of the bag (12) while extending to branch laterally from the gas guiding conduit (16, 34, 40) at a location remote from the breathing piece (28) and at least providing for being couplable to extend to a location of final discharging displaced from the location of use of the equipment (10) to limit the possibility of exhaled gas contamination of its zone of use; and in that at least part of the supply conduit (24), as appropriately couplable at its supply end, laterally meets the gas guiding conduit (16, 34, 40) also at a location remote from the breathing piece (28) thereby in conjunction with the conduit (20) contributing to facilitation of the use of the equipment (10) thereby limiting interference with a manual bag manipulation action once the equipment is in operative use.

2. Breathing equipment (10) at least employable for use in anesthesiology procedure comprising:

a regularly shaped breathing bag (12) of which its location of discharging of exhaled gas (12.2) is situated remote from its location (12.1) via which it is indirectly connectable to a patient and which is accordingly of a suitably flexible material to at least enable manually assisting in the breathing process of such patient during use of the equipment (10) in response to its manual compression and relaxation;

a gas-guiding conduit (16, 34, 40) extending between a breathing piece (28) via which gas is inhaled and exhaled by a patient during use of the equipment and the location (12.1) of the breathing bag (12);

a supply conduit (24) via which inhalation gas in the form of air or oxygen and, where applicable, agent is introduced for inhalation by such patient via the breathing piece (28); and a gas removal conduit (20) via which exhales gas is discharged;

characterized in that the gas removal conduit (20) comprises a bridging tube (18) returning in snug adjacent relationship with the breathing bag (12) from its location of discharging of exhaled gas (12.2) to the vicinity of the location (12.1) via which it is connectable to a patient by a quick release coupling that maintains proper access to the manual manipulation of the bag (12) and an exhaust gas conduit 22 branching laterally from the gas guiding conduit (16, 34, 40) at a location remote from the breathing piece (28) and at least providing for being couplable to extend to a location of final discharging displaced from the location of use of the equipment (10), to limit the possibility of exhaled gas contamination at the zone of use; and in that at least part of the supply conduit (24), as appropriately couplable at its supply end, laterally meets the gas guiding conduit (16, 34, 40) also at a location remote from the breathing piece (28) thereby in conjunction with the conduit (20) contributing to facilitation of the use of the equipment (10) thereby limiting interference with a manual bag manipulation action once the equipment is so in operative use.

3. Breathing equipment (10) at least employable for use in anesthesiology procedure comprising:

a regularly shaped breathing bag (12) of which its location of discharging of exhaled gas (12.2) is situated remote from its location (12.1) via which it is indirectly connectable to a patient and which is accordingly of a suitably flexible material to at least enable manually assisting in the breathing process of such patient during use of the equipment (10) in response to its manual compression and relaxation;

a gas-guiding conduit (16, 34, 40) extending between a breathing piece (28) via which gas is inhaled and exhaled by a patient during use of the equipment and the location (12.1) of the breathing bag (12);

a supply conduit (24) via which inhalation gas in the form of air or oxygen and, where applicable, agent is introduced for inhalation by such patient via the breathing piece (28); and a gas removal conduit (20) via which exhaled gas is discharged;

characterized in that the gas removal conduit (20) comprises a bridging tube (18) returning in snug adjacent relationship with the breathing bag (12) from its location of discharging of exhaled gas (12.2) to the vicinity of the location (12.1) via which it is indirectly connectable to a patient that maintains proper access to the manual manipulation of the bag (12) and an exhaust gas conduit 22 branching laterally from the gas guiding conduit (16, 34, 40) at a location remote from the breathing piece (28) and at least providing for being couplable to extend to a location of final discharging displaced from the location of use of the equipment (10), to limit the possibility of exhaled gas contamination at the zone of use; and in that at least part of the supply conduit (24), as appropriately couplable at its supply end, laterally meets the gas guiding conduit (16, 34, 40) also at a location remote from the breathing piece (28) thereby in conjunction with the conduit (20) contributing to facilitation of the use of the equipment (10) thereby limiting interference with a manual bag manipulation action once the equipment is so in operative use;

being further characterized in that the breathing equipment is assembled from a set at least comprising the breathing bag (12) formed with remotely situated gas flow connecting apertures, the exhaust gas discharge bridging conduit (18), the gas guiding tube (16), and a gas redirecting connector (14) along which a gas transfer and breathing bag discharging passage (34, 40) forming part of the gas guiding conduit is defined thus in conjunction with the gas guiding tube (16) forming the gas guiding conduit; and being so assembled into the breathing equipment (10) the connector (14) removably fitting between the end of the gas guiding tube (16) remote from that carrying the breathing piece (28) and the location (12.1) of the breathing bag (12) while further being constituted to in conjunction with the bridging conduit (18) and the exhaust conduit (22) define the gas removal conduit (20) and in addition also serving as a junction of introduction for the supply conduit (24) in the case of its passing along inside the exhaust conduit (22) and the gas guiding tube (16), exhaled gas from the gas guiding tube (16), once the equipment (10) is in use, passing through the breathing bag discharge passage (34, 40) and along the breathing bag and the bridging conduit (18) while returning via the connector (14) to the exhaust conduit (22).

4. Breathing equipment as claimed in claim 3 in which the connector (14) is in the form of a gas guiding and exhaust conduit connecting piece (30) removably socketing to a breathing bag inlet aperture connecting piece (42) to the effect of the gas transfer and breathing bag discharging passage (34, 40) extending centrally there along while accommodating a bridging conduit return sleeve (52) communicating via an exhaust conduit passage extending co-axially along a zone (46, 48) about the breathing bag discharge passage (34, 40) into the exhaust conduit (22).

5. A breathing equipment set assembleable into breathing equipment (10) at least employable for use in anesthesiology procedure comprising:

an oval shaped breathing bag (12) formed with remotely situated gas flow connecting apertures (12.1, 12.2);

a gas guiding tube (16) connectable to extend between a breathing piece (28) via which gas is inhaled and exhaled by a patient during use of such equipment (10) once assembled and the gas flow connecting aperture (12.1);

an exhaust gas discharge bridging tube (18) forming part of a gas discharge conduit (20) constituted once so assembled; and a gas redirecting connector (14) that is removably interspaceable between the end of the gas guiding tube (16) remote from the end to which the breathing piece (28) is connectable, and the inlet aperture end (12.1) of the breathing bag (12) to the distal end aperture (12.2) to which one end of the bridging conduit (18) is connectable;

the gas redirecting connector (14) being constituted to provide for the flow of exhaled gas from the gas guiding tube (16) via a gas transfer and breathing bag discharging passage (34, 40) along the connector (14) and along the breathing bag (12) and via the bridging conduit (18), as thus removably connected to the connector (14), and along a gas discharge zone of flow (46, 48) also formed along the connector (14) to an exhaust conduit (22) forming in conjunction with the bridging conduit (18) and the gas discharge zone (46, 48), such gas discharge conduit (20) while also serving as a bridging junction for an inhalation gas supply conduit (24), as thus extending along inside such exhaust conduit (22) as connected to the connector (14), and the gas guiding conduit (16) once the set is assembled into such equipment (10);

said breathing equipment set being further characterized by the connector (14) is in the form of a gas guiding and exhaust conduit connecting piece (30) removably socketable to a breathing bag inlet aperture connecting piece (42) to the effect of defining a centrally extending gas transfer and breathing bag discharging passage (34, 40) that extends between the gas guiding tube (16) and the breathing bag (12) once the pieces (30, 42) are interconnected and the set assembled into breathing equipment (10) while, when so interconnected, the connector (14) also forming the gas discharge zone of flow (46, 48) extending co-axially about the passage (34, 40) that is situated between the bridging conduit (18) and an exhaust conduit (22), once the set as appropriately supplemented, is thus assembled into such breathing equipment (10), for accommodating the return flow of exhaust gases from the conduit (18) to such exhaust conduit (22) by way of a bridging conduit return sleeve (52) forming the end of the bridging conduit (18) remote from that connectable to the aperture (12.2) from the bag (12) that is snugly receivable onto the upstream end of the zone of flow (46, 48).

6. A set as claimed in claim 5 that includes the breathing piece (28) incorporating a gas filter (62) downstream of the location of exhalation there into and upstream of the position of release of inhalation gas there into for promoting the unobstructed supply of inhalation gas to a patient while serving to filter exhaled gases once equipment (10) as assembled from the set is in use.

\* \* \* \* \*